United States Patent
Smith

(10) Patent No.: US 6,613,800 B1
(45) Date of Patent: Sep. 2, 2003

(54) METHOD AND COMPOSITIONS FOR TREATING PSORIASIS, ECZEMA, SEBORRHEA AND ARTHRITIS

(76) Inventor: Steven A. Smith, 5801 E. 41st, Ste 200, Tulsa, OK (US) 74135

(*) Notice: Subject to any disclaimer, the term of this patent is extended or adjusted under 35 U.S.C. 154(b) by 0 days.

(21) Appl. No.: 10/011,362

(22) Filed: Dec. 3, 2001

(51) Int. Cl.7 ..................... A61K 31/315; A61K 31/225
(52) U.S. Cl. ........................................ 514/494; 514/547
(58) Field of Search .................................. 514/494, 547

(56) References Cited

U.S. PATENT DOCUMENTS

| | | |
|---|---|---|
| 5,171,581 A | 12/1992 | Smith et al. |
| 5,433,954 A | 7/1995 | Smith et al. |
| 5,681,593 A | 10/1997 | Smith et al. |
| 5,716,646 A | 2/1998 | Smith et al. |
| 6,355,676 B1 * | 3/2002 | Joshi et al. ................ 514/494 |

* cited by examiner

Primary Examiner—Theodore J. Criares
Assistant Examiner—Jennifer Kim
(74) Attorney, Agent, or Firm—Molly D. McKay

(57) ABSTRACT

A method and composition for treating psoriasis, eczema, seborrheic dermatitis, and possibly arthritis. The present invention involves treatment of these conditions with an oral administration of a mixture comprised of three primary ingredients: fumaric acid and/or fumarate compounds, inorganic nickel compound(s) such as nickel sulfate, and inorganic bromide compound(s) such as potassium bromide.

3 Claims, No Drawings

METHOD AND COMPOSITIONS FOR TREATING PSORIASIS, ECZEMA, SEBORRHEA AND ARTHRITIS

CROSS-REFERENCE TO RELATED APPLICATIONS

Although this application is not a continuation of any previous patent, it employs a modification of the invention described in U.S. Pat. No. 5,433,954, which issued on Jul. 18, 1995. That patent is owned by the present Applicant, Steven A. Smith, and his wife, Loraine J. Smith, as co-inventors.

BACKGROUND OF THE INVENTION

1. Field of the Invention

The present invention relates to a method and composition for treating psoriasis, eczema, seborrheic dermatitis, and possibly arthritis. More specifically, the present invention involves treatment of these conditions with an oral administration of a mixture of fumaric acid, inorganic nickel compound(s), and inorganic bromide(s).

2. Description of the Related Art

Psoriasis is a chronic skin disorder that proliferates in nature and is widespread throughout the world, afflicting millions of humans and even afflicting domesticated animals having similar proliferative integument problems. The skin disorder is characterized by recurrent, elevated red lesions, plaques and on rarely pustules on the skin. These plaques are the result of an excessively rapid growth and shedding of epidermal or skin cells.

No one knows what causes this abnormal cell proliferation. Its severity and course vary greatly from case to case, and also vary in the individual afflicted with the disease. Recurrences are almost the rule with intervals varying from one month to many years. One person may go through life with a single patch on the elbow, knee or scalp, while another will have repeated attacks of a generalized eruption or widespread chronic lesions lasting for years without remission. As discouraging as it may be, medical science and literature are replete with indications that patients exhibiting such lesions are destined for life to be "psoriatic". With all of the advances in medical science, no one knows what causes this abnormal cell growth. With some of it, it is felt that some type of biochemical stimulus triggers this abnormal cell growth. It is still unknown whether the origin of this biochemical malfunction resides in the skin, in the immune system, in the white blood cells, or is possibly psychoneural. It is know that certain environmental factors can "trigger" the initial appearance or worsening of psoriasis. Conversely, the symptoms can spontaneously clear for reasons scientists do not understand. Treatment of the psoriasis is aimed at clearing the lesions for as long as possible. This is what is meant by the term 'remission" or "clearance". In any event, medical science has fairly well agreed that psoriasis is a heritable disease in which the specific defect seems to be unknown.

For years there have been many attempts to treat the disease, and several topical and systemic treatments for psoriasis which inhibit cell division have met with limited success in clearing the skin for short periods of time. Yet, the reason why these treatments work is not yet clearly understood. Treatments which have been suggested in the art appear to be symptomatic and palliative. Lesions may disappear spontaneously or as a result of the therapy, bur recurrences are likely. There is a tendency for each remedy gradually to lose its effectiveness or develop dangerous accumulative toxicity. Rarely, however, is the disease apparently cured, showing no evidence for years.

In the treatment of the disease, medical science has suggested low fat or low protein diets. Drugs such as systemic corticosteroids and ACTH are effective by limited to patients who are in great distress and do not respond to other measures. Such drugs may produce dangerous side effects; and in some instances, one the drugs are discontinued, the eruption may show a marked exacerbation. Folic acid antagonist have been found to have some beneficial treatment but are a dangerous form of therapy. Although other drugs have been suggested, for the most part the serious side effects associated therewith have not made them successful. Ionizing radiation therapy, e.g. grenz-ray treatment, has provided only temporary benefit, but the dangers of addiction to such radiation producing radiodermatitis and subsequent carcinoma is not worth continued treatment. Corticosteroid ointment in combination with polyethylene film has had some success, but systemic effects may be caused by extensive use. Ointments have been found to be more beneficial than lotions. A typical ointment may contain anthralin or tar. Hydrophilic ointment containing salicylic acid and sulfur is also found to be beneficial, especially for scalp treatment. Again, the side effects and the absorption within the human system of these chemicals must be guarded. Other treatments including sunlight baths or ultraviolet (UV) baths with the lesions painted with a solution of coal tare, anthralin or psoralens have been found to be helpful.

Ongoing studies in the art concern the use of vitamin $D_3$ (1, 25-dihydroxivitamin $D_3$). Etretin and Etretinate are new generation retinoids presently being studied for treating psoriasis, but again, the side effects must be carefully monitored.

Other ongoing studies include the use of the drug cyclosporine, RS 53179 (a non-steroidal, anti-inflammatory drug), fish oil, hypothermia, and anti-yeast agents.

One method for alleviating psoriasis is taught in U.S. Pat. No. 4,181,725 which teaches a pharmaceutical compound which contains as its active components at least on compound selected from the group consisting of parabromophenacyl bromide, alpha tocopherol, mepacrine, chloroquine, hydroxychloroquine, dibucaine, tetracaine, lidocaine, butacaine, procaine, ethylene diamine tetra, acetic acid, and ethylene glycol bis (β amino ethyl ether) -N-N'tetraacetic acid within a suitable carrier.

Seborrheic dermatitis (seborrhea) in the least severe form, but most common, is simple dandruff. It can become more severe and form scaly, red patches on the face, ears, chest, and other widespread areas. It often coexists with psoriasis, and many subjects have overlapping features termed "seborrhiasis". Therefore, a continuum may exist whereby these are on the same disease spectrum. Treatments are similar to those currently used for psoriasis, although lower dosages are usually sufficient to control seborrheic dermatitis.

Eczema (including but not limited to atopic, nummular and hand types) often has similar overlapping features with psoriasis. See, e.g., H. Roenigk, Jr. et al., "Psoriasis", © 1991, Marcel Dekker, Inc., Chapter 2. For instance, it is often difficult to distinguish based on clinical appearance. They can coexist, or the disease can begin as eczema and over time turn to psoriasis. Again, treatments are similar with corticosteroids and tar preparations commonly employed for both of these conditions.

Similar conditions to both seborrheic dermatitis and eczema also occur in various domestic animals (mange, etc.). The current invention is felt to encompass all similarly involved species.

Seborrheic dermatitis and eczema have several other features in common with psoriasis. They are very common in the general population. They have no known cause, although many theories are advanced. They have no known cure, although many similar temporary remedies are known. All of these conditions are known to worsen with stress. Finally, there seems to be a hereditary basis or tendency for development of each of these skin diseases, although this is not a strict finding.

U.S. Pat. No. 5,433,954 teaches the desirability of treating psoriasis, seborrheic dermatitis, and eczema with a composition containing inorganic nickel compounds and inorganic bromide compounds. Although some European doctors have advocated use of very high dosages of fumaric acid to treat patients with psoriasis, the dosages advocated by these proponents are dangerously high.

Applicant has found that in treating particularly resistant cases of psoriasis, seborrheic dermatitis, and eczema, a composition including nickel, bromide, and a fairly low dosage of fumaric acid has proved to be more effective than either the nickel and bromide composition taught in U.S. Pat. No. 5,433,954 or a low dosage of fumaric acid alone. Case studies show that there appears to be a synergistic effect when a low dosage of fumaric acid is used in combination with nickel and bromide to treat these diseases.

Also, although Applicant has not conducted sufficient testing to confirm the effectiveness of this same treatment on patients suffering from arthritis, Applicant is hopeful that this same type of treatment may likewise prove useful for treating this arthritis.

SUMMARY OF THE INVENTION

The present invention relates to a method and composition for treating psoriasis, eczema, seborrheic dermatitis, and possibly arthritis. More specifically, the present invention involves treatment of these conditions with an oral administration of a mixture comprised of three primary active ingredients: fumaric acid, inorganic nickel compound(s), and inorganic bromide compound(s).

The specific composition preferably contains three active ingredients: an inorganic nickel salt such as nickel sulfate, an inorganic bromide salt such as potassium bromide, and fumaric acid.

Generally, the preferred dosage range for nickel is 0.023–0.083 mg/kg of body weight/day; the preferred dosage range for bromide is 0.344–1.238 mg/kg of body weight/day; and the preferred dosage range for fumaric acid is 1.375–4.950 mg/kg of body weight/day. Clinical tests have shown the following dosage to be effective: from about 1–135 mg bromide/day and from about 0.1–12 mg nickel/day and from about 4–270 mg fumaric acid/day. Alternately, fumarate at a dosage of about 15–360 mg fumarate/day has been effectively substituted for the fumaric acid. Although testing is not completed, it is believed that the following dosage is effective: from about 0.1–1000 mg bromide/day and from about 0.01–100 mg nickel/day and from about 1–1000 mg fumaric acid/day. Alternately, it is believed that about 1–1000 mg fumarate/day may be substituted for the fumaric acid. The fumarate employed in all these dosages is either monoethyl fumarate or dimethyl fumarate or a combination of both compounds.

DETAILED DESCRIPTION OF THE PREFERRED EMBODIMENT

THE INVENTION

The present invention relates to a method and composition for treating psoriasis, eczema, seborrheic dermatitis, and possibly arthritis. More specifically, the present invention involves treatment of these conditions with an oral administration of a mixture comprised of three primary active ingredients: fumaric acid, inorganic nickel compound(s), and inorganic bromide compound(s).

The specific composition is preferably made into a tablet form and contains three active ingredients: an inorganic nickel salt such as nickel sulfate, an inorganic bromide salt such as potassium bromide, and fumaric acid. The homeopathic form of fumaric acid is preferred, although fumarate forms, i.e. salt forms of fumaric acid, such as for example monoethyl fumarate and dimethyl fumarate, may also prove to be effective. Each 600 mg tablet contains the three active ingredients at the calculated drug strength as follows: 1× or 2.6 mg. of nickel sulfate which is approximately 1.0 mg. of ionic nickel, 1× or 22 mg. of potassium bromide which is approximately 15 mg. of bromide, and 1× or 30 mg of fumaric acid. The inactive ingredients used in the tablets may be any of a variety of ingredients, but lactose and magnesium stearate have been successfully used.

Absorption of nickel sulfate is variable among individuals. For maximum absorption, the tablets should preferably be taken orally at the beginning of the day on an empty stomach or at any convenient time after having taken nothing but water for at least 7 hours. It is also recommended that the patient take nothing by mouth except water for 1 hour after taking the tablets to further aid in absorption. The tablets may be chewed, swallowed or dissolved under the tongue.

The preferred dosage range is given below for various patient weights. Generally, the preferred dosage range for nickel is 0.023–0.083 mg/kg of body weight/day; the preferred dosage range for bromide is 0.344–1.238 mg/kg of body weight/day; and the preferred dosage range for fumaric acid is 1.375–4.950 mg/kg of body weight/day.

| Patient Weight (lbs.) | Starting Dose (tablets) | Max. Dose (tablets) |
| --- | --- | --- |
| 40–80 | ½ | 1½ |
| 80–120 | 1 | 3 |
| 120–160 | 1½ | 4½ |
| 160–200 | 2 | 6 |
| 200–240 | 2½ | 7½ |
| Over 240 | 3 | 9 |

The conversion factor for converting pounds of patient body weight into kilograms of patient body weight is 2.2 lbs.=1 kg.

Dosages in the following ranges have been shown effective in clinical tests on human patients: from about 1–135 mg bromide/day and from about 0.1–12 mg nickel/day and from about 4–270 mg fumaric acid/day. Alternately, the following dosage ranges have been shown effective in clinical tests on human patients when fumarate is employed instead of fumaric acid: from about 1–135 mg bromide/day and from about 0.1–12 mg nickel/day and from about 15–360 mg fumarate/day. The fumarate employed in these tests is either monoethyl fumarate or dimethyl fumarate or a combination of both compounds.

Although clinical tests have not yet been conducted, it is believed that the following dosage ranges are effective in treating human patients for psoriasis, eczema, seborrhea and arthritis: from about 0.1–1000 mg bromide/day and from about 0.01–100 mg nickel/day and from about 1–1000 mg fumaric acid/day to said patient. Alternately, the following dosage ranges are believed to be effective on human patients when fumarate is employed instead of fumaric acid: from about 0.1–1000 mg bromide/day and from about 0.01–100 mg nickel/day and from about 1–1000 mg fumarate/day to said patient. Again, the fumarate employed is either monoethyl fumarate or dimethyl fumarate or a combination of both compounds.

CASE STUDIES

The following case studies are presented to show results from clinical trials of the present invention on resistant cases of psoriasis, eczema and seborrhea. Although clinical trials of the present invention on arthritis cases are not completed, early indications show that this treatment may also have therapeutic value in treating arthritis.

A combination of Psorizide Ultra® and Psorex® was employed in some of these case studies. In others, a combination of Psorizide Ultra® and Fumaric Acid 1× was used. Psorizide Ultra® is a natural mineral homeopathic medication commercially available from Applicant's company, i.e. LOMA LUX Laboratories, 5801 E. 41$^{st}$ Street, Suite 200, Tulsa, Okla. 74135. This prescription drug includes active ingredients of nickel sulfate and potassium bromide.

Psorex® is a scientifically designed supplement containing reagent grade fumaric acid esters. This supplement is commercially available from Ecological Formulas at 1-800-888-4585. Each Psorex® capsule contains 120 mg fumaric acid ester.

Fumaric Acid 1×300 mg tablets are commercially available from B.H.I., 11600 Cochiti Road SE, Albuquerque, N.Mex. 87123-3376. Each Fumaric Acid 1× tablet contains approximately 30 mg of fumaric acid.

Case No. 1

The patient is a 61 year old man who developed blistering scaly fissuring eczema on his hands and feet in 1999 and was treated initially with Prednisone® oral therapy. He was seen by a dermatologist from March 2000 through May 2000 and treated with varying potent and super potent topical corticosteroids with variable results. He was seen on June 2000 by Applicant with hands and feet skin "breaking open and splitting, very painful". He was treated with Psorizide Ultra® two tablets every morning. He was also given Erythromycin® 250 mg. bid for ten days and Bactroban® Ointment with 5% Sulfur in Triamcinalone® Ointment 0.1%.

He was seen again one month later "doing good" with healing fissures on skin of hands and feet. Psorizide Ultra® two tablets daily were continued and Psorex® two capsules daily were added. Various topical ointments were also used.

One month later (August 2000) the hands were much improved (practically clear) and only one small fissure was left on the feet. Therapy was continued until two months later when his cardiologist took him off the oral skin medication. His hand and foot eczema gradually worsened on topical therapy.

Case No. 2

The patient is a 70 year old man with a three year history of body eczema. He was seen by dermatologists many times for severe flaring extensive skin itching and redness. He was treated with oral antibiotics, antifungal and corticosteroids (as well as many topical agents) with variable results.

He was seen by Applicant July 2000 with new areas on legs and "deep itching in the skin". The exam showed eczematous red pruritic papules and plaques with crusting on both hips, upper body, and arms. Treatment was given with Psorizide Ultra® two tablets daily and Psorex® two capsules daily. Kenalog® 20 mg IM was also given.

Patient was seen August 2000 and was "doing very well". All lesions were very faded to clear. Therapy was continued.

Patient did well until September 2001 despite going off of therapy for some time. He then complained of itching behind the ears and scalp. His skin showed a mild dry texture. Psorizide Ultra® two tablets and Fumaric Acid 1× two tablets were given daily.

Case No. 3

The patient is a 68 year old man with a ten year history of psoriasis of the anogenital region. He had been treated with numerous topical lotions with only limited results. More recently he also developed left knee involvement and flaring of all disease sites due to surgery. He presented November 2000 complaining of itching. Exam showed red scaly lesions widespread including upper back and shoulders, buttocks and groin/genitals, face, scalp, and ankles. Psorizide Ultra® two tables and Psorex® two capsules were started daily. Temovate® E Cream and Triamcinalone® 0.1% Cream were continued and 1 cc of Vitamin B-12 was given I.M.

Six days later itching was gone and some skin areas were getting better. Exam showed small faded papules on forearms, mild red patches in axilla and faded patches on left kneed. Therapy was continued.

Case No. 4

The patient is a 51 year old woman with a two year history of seborrhea. She was treated for red scaly itchy scalp in July 2000 with Psorizide Ultra® two tablets daily and Kenalog® spray as needed.

She returned for follow up October 2000 and was improved with no scale or build up on scalp. Therapy was continued and Psorex® one capsule daily was started.

Follow-up in November 2000 revealed the scalp was clear, and therapy was continued. Exam March 2001 showed the entire scalp looked healthy.

Case No. 5

The patient is a 25 year old woman with a long history of extensive plaque psoriasis. In October 2000 she was getting worse. Exam showed increasing plaques from scalp to the mid back area. Psorizide Ultra® two tablets daily was continued and Psorex® ½ capsule daily was started. Topical therapy consisted of Kenalog® spray, Dovonex® Solution, Emboline® E cream and 10% L.C.D. in Aquaphor®.

In November 2000 her disease was stable and therapy was continued.

In December 2000 her psoriasis was "doing pretty good". A small red patch on left frontal scalp and numerous small thin plaques were found on her back. Therapy was continued and Psorex® was increased to one capsule daily.

She was seen March 2001 and doing even better. Therapy was continued. In May 2001 she was again doing better. During the summer of 2001 she completely cleared for three weeks, but she ran out of medication and the psoriasis recurred.

In September 2001 she had papules on the elbows, thin plaques on the occipital scalp and some involvement of the trunk. Psorizide Ultra® three tablets and Fumaric Acid 1× three capsules daily were prescribed.

Case No. 6

The patient is a 12 year old girl with a two year history of scalp psoriasis. She was initially treated with topicals, but returned November 2000 with flaring. Exam showed moderately thick plaques in the scalp and in and around the ears. Loma Lux Psoriasis® 5 ml and Psorex® one capsule daily were administered. Various topical therapies were given also. Loma Lux Psoriasis® is the liquid, over the counter form of Psorizide Ultra® also available commercially from LOMA LUX Laboratories, 5801 E. 41$^{st}$ Street, Suite 200, Tulsa, Okla. 74135.

In December 2000 she was doing better with decreasing amounts of scalp and ear psoriasis. Therapy was continued and follow-up in January 2001 showed continued improvement with only small right ear involvement and mild patches in scalp. Itching was improved and rated as mild. Therapy was continued.

Case No. 7

The patient is a 16 year old mentally handicapped young woman who has a long history of psoriasis which was difficult to control She presented July 2000 flaring with widespread disease on the face, trunk and extremities. Numerous small plaques and papules covered large areas of her body. Psorizide Ultra® one tablet and Psorex® one capsule were started daily. Topical therapies were also given.

In August 2000 she returned with considerable fading and thinning of all lesions. She was responding well and therapy was continued the same except to increase Psorex® to two capsules per day.

In October 2000, the patient was even more improved with just a moderated sized patch on the scalp. Faded papules existed on the extremities. Therapy was continued and patient remained fairly stable with trunk, scalp and face relatively clear and numerous thin small lesions on the extremities.

In September 2001 she was still stable and therapy continued on Psorizide Ultra® two tablets daily. Psorex® was discontinued and Fumaric Acid 1× two tablets daily was begun.

Case No. 8

The patient is a 51 year old man with a nine year history of psoriasis. He went into remission in 2000, but it recurred in 2001. He presented in August 2001 with six months of flaring disease. Elbows and knees had large thick plaques, and the back, legs, ears and groin had smaller plaques. Psorizide Ultra® three tablets and Furmaric Acid 1× three tables were started. A variety of topical therapies were also started.

In September 2001 patient returned showing improvement with central clearing and thinning of all lesions. Therapy was continued.

Case No. 9

The patient is a 32 year old man with a 13 year history of extensive plaque psoriasis. In November 2000 his skin showed forearms, scalp and facial red scaly thin plaque with a few areas of involvement on trunk and legs. Psorizide Ultra® three tablets and Psorex® one tablet daily were given along with topical therapy.

In December 2000 his plaques were thinning into patches. In January 2001 he was doing well on the same therapy. His scalp involvement was improving nicely and rated as very mild patches. Therapy was continued.

In March 2001 he was stable with small faded patches on the face and scalp with thin plaques on the forearms, elbows, and scalp. Psorex® was stopped at this time.

In April 2001 Methotrexate® 5–10 mg per week was started. He reported doing very well through the summer, but by August 2001 the psoriasis was worse. At that time exam showed small red papules and plaques on the forehead and mild red scaling patches behind both ears and on the scalp. Psorizide Ultra® four tablets and Fumaric Acid 1× four tables were given along with topical therapy. Methotrexate® was discontinued.

Case No. 10

The patient is a 64 year old woman with several year history of hand and foot psoriasis. In November 2000 she had thickened scaly plaques on the palms and soles with deep pustules. Psorizide Ultra® two tablets and Psorex® one capsule daily were started along with Erythomycin® 250 mg bid and topical therapy.

In December 2000 she was improved with only one pustule on left palm and shrinking areas and severity on both palms and soles. Therapy was continued.

In January 2001 she returned with some worsening. Three pustules were found on left palm with increased itching. Other parameters were stable.

In August 2001 she had gotten bad again and was only using topical agents. Exam showed scaling and thickening and deep seated vesicles on the palms. Soles, heals and ankles showed severe involvement with some microvesicles. Psorizide Ultra® two tablets and Fumaric Acid 1× two tablets were started. She was also treated with Buspar® 10 mg bid and Doxeprin® 10 mg ghs. Topical therapy was continued.

In September 2001 she was improved with tiny pustules and resolving vesicles on left heel and palms. There was only mild redness and scale remaining on palms and feet. Psorizide Ultra® two tablets and Fumaric Acid 1× three tablets were given. Other therapy was continued.

Case No. 11

The patient is a 48 year old woman with a several year history of psoriasis. She was seen August 2001 with enlarging blistering disease. Exam showed vesicles and crusting on fingers of left hand with mild dry patches on right hand and right lower leg/ankle. Thin plaque was on left elbow. Psorizide Ultra® two tablets and Fumaric Acid 1× two tablets daily were started along with topical therapy.

In September 2001 she was improved with only one vesicle on left hand and right hand was clear. Psorizide Ultra® two tablets and Fumaric Acid 1× three tablets daily and Erythomycin® 250 my bid were given.

The examples provided above are not meant to be exclusive. Many other variations of the present invention would be obvious to those skilled in the art, and are contemplated to be within the scope of the appended claims, including the full range of equivalency to which each element thereof is entitled.

Also, although the invention has been described as orally administered, the invention is not so limited and may be administered topically or by any other suitable means of administration.

What is claimed is:

1. A method of treating psoriasis, eczema, seborrhea and arthritis in a human patient comprising administering synergistic effective amounts from about 0.023–0.083 mg nickel/kg of body weight/day and from about 0.344–1.238 mg bromide/kg of body weight/day and from about 1.375–4.950 mg fumaric acid/kg of body weight/day to said patient.

2. A method of treating psoriasis, eczema, seborrhea and arthritis in a human patient comprising simultaneously administering synergistic effective amounts from about 1–135 mg bromide/day and from about 0.1–12 mg nickel/day and from about 4–270 mg fumaric acid/day to said patient.

3. A method of treating psoriasis, eczema, seborrhea and arthritis in a human patient comprising simultaneously administering synergistic effective amounts from about 0.1–1000 mg bromide/day and from about 0.01–100 mg nickel/day and from about 1.0–1000 mg fumaric acid/day to said patient.

* * * * *